(12) United States Patent
Müller et al.

(10) Patent No.: US 6,221,577 B1
(45) Date of Patent: Apr. 24, 2001

(54) SEROREACTIVE REGIONS ON HPV 16-PROTEINS E1 AND E2

(75) Inventors: Martin Müller, Heidelberg; Lutz Gissmann, Wiesloch, both of (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/468,337

(22) Filed: Jun. 6, 1995

Related U.S. Application Data

(62) Division of application No. 08/237,418, filed on May 3, 1994, now Pat. No. 5,601,973, which is a continuation of application No. 07/913,613, filed on Jul. 16, 1992, now abandoned.

(30) Foreign Application Priority Data

Jul. 18, 1991 (DE) .................................................. 41 23 760

(51) Int. Cl.$^7$ ........................... C12Q 1/70; A61K 39/12; A61K 38/00; C07H 21/04
(52) U.S. Cl. .......................... 435/5; 435/7.94; 435/7.95; 424/185.1; 424/186.1; 424/204.1; 530/300; 530/325; 530/326; 530/327; 536/23.72; 930/220
(58) Field of Search .................... 424/204.1, 185.1, 424/186.1; 514/2; 530/300, 350, 324, 325, 326, 327; 930/220; 435/5, 7.94, 7.95; 536/23.72

(56) References Cited

U.S. PATENT DOCUMENTS 4,554,101 * 11/1985 Hopp .
5,180,806 * 1/1993 Dillner et al. .

FOREIGN PATENT DOCUMENTS

0257754 A2 * 3/1988 (EP) .
0344940 A2 * 12/1989 (EP) .
91/18294 * 11/1991 (WO) .

OTHER PUBLICATIONS

Kochel et al, 1991, Virology, vol. 182, pp. 644–654.*
J. Dillner, Mapping of Linear Epitopes of Human Papillomavirus Type 16: the E1, E2, E4, E5, E6 and E7 Open Reading Frames, Int. J. Cancer, 46:703–711 (1990).*
A.J.Cumber et al., Preparation of Antibody–Toxin Conjugates, Methods in Enzymology, 112:207–225 (1985).*
M. Duerst et al., A Papillomavirus DNA From a Cervical Carcinoma and Its Prevalence In Cancer Biopsy Samples From Different Geographic Regions, Proc. Natl. Acad. Sci. USA, 80:3812–3815 (1983).*
Lees, E.M. et al., The E2 Protein of Human Papillomavirus Type 16, Eur. J. Biochem. 190:85–92 (1990).*
J.M. Gauthier et al., Structural Analysis of the Human Papillomavirus Type 16–E2 Transactivator with Antipeptide Antibodies Reveals a High Mobility Region Linking the Transactivation and the DNA–Binding Domains, Nucl. Acid Res. 19(25):7073–7079 (1991).*
R.W. Ellis, New Technologies for Making Vaccines, 568–575 (1988).*
Human Papillomavirus Type 16 DNA Sequence, K. Seedorf et al., Virology 145:181–185 (1985).*
Filamentous Fusion Phage: Novel Expression Vectors That Display Cloned Antigens On the Virion Suface, G. Smith, Science, 228:1315–1316 (1985).*
Antibody–Selectable Filamentous fd Phage Vectors: Affinity Purification of Target Genes, S. Parmley et al., Gene 73:305–318 (1988).*
Filamentous Phages As Cloning Vectors, G. Smith, Survey of the Uses of F1 Phage Vectors, 3:61–83 (1987).*
Gene–III Protein of Filamentous Phages: Evidence for a Carboxyl–Terminal Domain With a Role In Morphogenesis, J. Crissman et al., Virology 132:445–455 (1984).*
Identification of Early Proteins of the Human Papilloma Viruses Typed 16 (HPV 16) and Type 18 (HPV 18) In Cervical Carcinoma Cells, K. Seedorf et al. The EMBO Journal 6:(1) 139–144 (1987).*
Plasmid Vectors For High–Efficiency Expression Controlled By the PL Promoter of Coliphage Lambda, E. Remaut et al., Gene 15:81–93 (1981).*
The Genetic Map of the Filamentous Bacteriophage f1, L. Lyons et al., Virology 49:45–60 (1972).*

* cited by examiner

*Primary Examiner*—Ali Salimi
(74) *Attorney, Agent, or Firm*—Finnegan, Henderson, Farabow, Garrett and Dunner, L.L.P.

(57) ABSTRACT

The invention relates to seroreactive regions on protein E1 and E2 of human papillomavirus (HPV) 16. The application also relates to a vaccine which contains such peptides which contain the seroreactive regions. The invention likewise embraces compositions for diagnostic purposes which contain peptides with the seroreactive regions.

44 Claims, 5 Drawing Sheets

| CLONE | SEQUENCE | POSITION | ISOLATE |
|---|---|---|---|
| REGION E1-1090: | | | |
| 1090 | NGMFYVEAVVEKKTGDAISDDENENDSDTGEDLVDFIVNDNDYLT | AS 16-60 | 1 |
| 1079 | NENDSDTGEDLVDFIVND | AS 38-55 | 3 |
| 1084 | MADPAGTNGEEGTGCNGMFYVEAVVEKKTGDAISDDENENDSDTGEDLVDFIVNDNDYLT | AS 1-60 | 3 |
| 1029 | EDLVDFIVNDNDYLT | AS 46-60 | 5 |
| 1099 | EDLVDFIVNDNDYLTQAETETAHALFTAQEAKQH | AS 46-79 | 5 |
| 1145 | NENDSDTGEDLVDFIVNDNDYLTQAETETAHALFTAQEAKQHRDAVQVLKRKYLvvh | AS 38-91 | 1 |
| REGION E1-1059: | | | |
| 1059 | stgsktkvfGSPLSDIS | AS 92-99 | 1 |

FIG. 2

| CLONE | SEQUENCE | POSITION | ISOLATE |
|---|---|---|---|
| REGION E2-1066: | | | |
| 1066 | DKILTHYENDS | AS 13-23 | 3 |
| 1025 | DKILTHYENDSTDLRDHI | AS 13-30 | 5 |
| REGION E2-1170: | | | |
| 1170 | DLRDHIDYWKH | AS 25-35 | 2 |
| REGION E2-1074: | | | |
| 1074 | AIYYKAREMGFKHINHQVPTLA | AS 41-63 | 4 |
| 1060 | AIYYKAREMGFKHINHQVPTLAVSKNKAL | AS 41-70 | 2 |
| 1061 | YYKAREMGFKHINHQVPTLAVSKN | AS 43-67 | 1 |
| 1063 | INHQVPTLAVSKNKALQAI | AS 55-73 | 1 |
| 1057 | INHQVPTLAVSKNKAL | AS 55-70 | 4 |
| 1018 | TLAVSKNKALQAIELQLTLETIYNSQYSNEKWTLQDV | AS 61-76 | 2 |
| REGION E2-1112: | | | |
| 1112 | QLTLETIYNSQYSNEKWTLQDVSLE | AS 76-100 | 1 |
| 1156 | TLETIYNSQYSNEK | AS 78-91 | 1 |
| REGION E2-1158: | | | |
| 1158 | TSVFSSNEVSSPEII | AS 197-211 | 1 |
| 1121 | VFSSNEVSSPEIIRQHLANHPAATHTKAVALGTEET | AS 199-234 | 2 |
| REGION E2-1102: | | | |
| 1102 | EIIRQHLANHPAATHTKAVALGTEETQTTIQPPRSEP | AS 209-245 | 1 |
| 1091 | TEETQTTIQPPRSEPDTGN | AS 231-249 | 2 |

FIG. 5

SEROREACTIVE REGIONS ON HPV 16-PROTEINS E1 AND E2

CROSS REFERENCE TO RELATED APPLICATIONS

This is a division of application Ser. No. 08/237,418 filed May 3, 1994 now U.S. Pat. No. 5,601,973 which is a continuation of application Ser. No. 07/913,613 filed Jul. 16, 1992, abandoned, which claims the right of foreign priority under 35 U.S.C. § 119, from an application P 41 23 760.9 filed in the Federal Republic of Germany on Jul. 18, 1991.

The invention relates to seroreactive regions on proteins E1 and E2 of human papillomavirus (HPV) 16.

The application also relates to a vaccine which contains such peptides which contain the seroreactive regions.

The invention likewise embraces compositions for diagnostic purposes which contain peptides with the seroreactive regions.

HPV 16 is one of the human papillomaviruses (Proc. Natl. Acad. Sci., USA 80, 3813–3815 (1983). The organization of the genome of HPV 16 has been described in Virology 145, 181–185 (1985).

Genomic sequences of HPV can be detected in most cases of preinvasive and invasive cervical tumors. HPV 16 has been identified world-wide as the virus type predominating in these tumors. The HPV 16 genome is detectable in more than 50% of cervical tumors, in which case it is often present integrated into the cellular DNA. Little is known about the immune response after infections with HPV 16 or other papillomaviruses.

Initial data: patients suffering from cervical tumors were compared with healthy individuals with regard to the presence of antibodies against viral proteins. These viral proteins were then linked as fusion products with various prokaryotic peptides at their N terminus and then used as antigens in Western blots.

The object of the present invention is the further identification of HPV 16 viral structures which can be used as tool in the prophylaxis, diagnosis and therapy of HPV 16-dependent tumorous diseases in humans. The identification of such structures is a prerequisite for the development of ELISAs which make it possible to test a large quantity of human sera for the presence of HPV 16.

The present invention therefore embraces seroreactive regions of the E1 protein of HPV 16, which have one of the following amino-acid sequences:

| | | |
|---|---|---|
| I. | NGWFYVEAVVEKKTGDAISDDENENDSDTGEDLVDFIVNDNDYLT | (SEQ ID NO: 1) |
| II. | NENDSDTGEDLVDFIVND | (SEQ ID NO: 2) |
| III. | MADPAGTNGEEGTGCNGWFYVEAVVEKKTGDAISDDENENDSDTGEDLVDFIVNDNDYLT | (SEQ ID NO: 3) |
| IV. | EDLVDFIVNDNDYLT | (SEQ ID NO: 4) |
| V. | EDLVDFIVNDNDYLTQAETETAHALFTAQEAKQH | (SEQ ID NO: 5) |
| VI. | NENDSDTGEDLVDFIVNDNDYLTQAETETAHALFTAQEAKQHRDAVQVLKRKYL | (SEQ ID NO: 6) |
| VII. | GSPLSDIS; | (SEQ ID NO: 7) | seroreactive regions of the E2 protein of HPV 16, which have one of the following amino-acid sequences:

| | | |
|---|---|---|
| I. | DKILTHYENDS | (SEQ ID NO: 8) |
| II. | DKILTHYENDSTDLRDHI | (SEQ ID NO: 9) |
| III. | DLRDHIDYWKH | (SEQ ID NO: 10) |
| IV. | AIYYKAREMGFKHINHQVVPTLA | (SEQ ID NO: 11) |
| V. | AIYYKAREMGFKHINHQVVPTLAVSKNKAL | (SEQ ID NO: 12) |
| VI. | YYKAREMGFKHINHQVVPTLAVSKN | (SEQ ID NO: 13) |
| VII. | INHQVVPTLAVSKNKALQAI | (SEQ ID NO: 14) |
| VIII. | INHQVVPTLAVSKNKAL | (SEQ ID NO: 15) |
| IX. | TLAVSKNKALQAIELQLTLETIYNSQYSNEKWTLQDV | (SEQ ID NO: 16) |
| X. | QLTLETIYNSQYSNEKWTLQDVSLE | (SEQ ID NO: 17) |
| XI. | TLETIYNSQYSNEK | (SEQ ID NO: 18) |
| XII. | TSVFSSNEVSSPEII | (SEQ ID NO: 19) |
| XIII. | VFSSNEVSSPEIIRQHLANHPAATHTKAVALGTEET | (SEQ ID NO: 20) |
| XIV. | EIIRQHLANHPAATHTKAVALGTEETQTTIQRPRSEP | (SEQ ID NO: 21) |
| XV. | TEETQTTIQRPRSEPDTGN. | (SEQ ID NO: 22) |

The invention furthermore embraces peptides with one or more of the seroreactive regions identified above, a vaccine which contains one or more of the peptides identified above, a composition for diagnostic purposes for the identification of specific antibodies against HPV E1 and/or E2 protein, which likewise contain the peptides identified above, and monoclonal antibodies which have an affinity for one or more of the seroreactive regions of the E1 or E2 protein of HPV 16, and a composition for diagnostic purposes which contains these monoclonal antibodies.

In order to identify seroreactive regions in proteins E1 and E2 of HPV, the experimental route described in Science 228, 1315–1317 (1985) was followed. Subgenomic HPV 16 DNA fragments which had been randomly generated by ultrasound treatment and partial DNAse I treatment were cloned into the phage vector fuse1 and then expressed as part of a phage coat protein. Seroreactive phage recombinants were identified using sera prepared against E1 and E2, and purified, and the seroreactive regions were characterized by sequencing the HPV 16 portion. Polyclonal rabbit sera against an HPV 16 E1 MS2 polymerase fusion protein and against the amino- and carboxyl-terminal part of HPV 16 E2 (separate, likewise MS2 fusion proteins) were prepared.

The filamentous phages embrace the three groups f1, fd and M13. It is common to them all that binding and uptake of the phages takes place via F pili of the bacteria, i.e. that only $F^+$ strains can be infected. The fd wild-type phage, from which the vector system used is derived, forms particles which are about 900×6 nm in size and which are composed in particular of about 2700 subunits of the main coat protein. In addition, in each case 5 molecules of the minor coat proteins pIII, pVI, pVII and pIX are located at both ends of the virions. The single-stranded, circular phage genome which, in the case of the fd wild-type, is 6408 bp in size, carries the information for a total of 10 different proteins.

In the fd derivatives fuse1, fuse2 (Parmley and Smith, Gene, 7, 305–318 (1988)) and fusemm, a tetracycline-resistance gene is integrated, by insertion of a part of the Tn10 transposon, in the phage genome, which has been enlarged to about 9.2 kbp in this way. This means that the replicative DNA double-stranded phage genomes behave in the bacteria like selectable plasmids and can accordingly be prepared and used for clonings. Another modification from the wild-type is the presence of a reading frame mutation in the gene for the minor coat protein pIII in conjunction with an inserted restriction site for cloning expressable DNA fragments. The gene for pIII is composed of two almost completely independent domains (Crissmann and Smith, 1984): an N-terminal domain which mediates the binding of the phages to the bacterial cell receptor (F pili) and a C-terminal protein domain which is responsible for phage morphogenesis. The reading frame mutation, which is located directly behind the signal sequence of the protein, thus leads to inactivation of the gene and accordingly also prevents the formation of infectious particles. This is of importance for the replication of these phage mutants as plasmids because the fd genomes inactivated in the morphogenesis do not damage the host bacteria (Smith, in: Vectors, A Survey of Molecular Cloning Vectors and Their Uses, Butterworth Publishers, Stoneham, Mass. 61–85, 1987).

Insertion of suitable DNA fragments and restoration of gene III functions lead to the formation of infectious phage particles which carry additional amino-acid sequences on their coats. These sequences are accessible to various ligands, for example antibodies, in the natural state of the phages.

The fd expression system used in this invention is essentially based on setting up phage banks by cloning DNA foreign sequences into the gene III, and examining the latter with the aid of monoclonal or polyclonal sera for seroreactive recombinants. An amplification normally takes place on preparation of these expression banks. The extent of this replication of individual clones in turn depends on the nature and size of the inserted DNA sequence. This means that different clones differ in frequency, which may differ by up to several powers of ten. It is therefore possible to derive from the stated properties the following two features of the fd expression banks:

Amplification of the banks, which leads to repeated cloning of identical phage clones isolated by immunoscreening.

Possibility of enriching seroreactive phages by affinity chromatography (columns) because phages in the active state can be bound and eluted again.

The repeated isolation of identical recombinants was avoided by using separately set up banks, there being an extremely low probability of cloning a DNA fragment prepared identically and in parallel, or of the phage recombinant derived therefrom.

In this invention, a total of 11 different expression banks for HPV 16 DNA in fuse1 were set up. The number of primary, tetracycline-resistant and insert-harbouring recombinants was in this case between 2000 and 90000 per bank. Since complete plasmids composed of about 4 kb vector portion and 8 kb HPV portion in sheared form were always used for the cloning, the HPV-containing fd recombinants are reduced by about 30%. The fragments cloned in were then expressed, as already mentioned, as fusion protein of the gene III coat protein. The cloning site in the gene III is in this case directly behind the translated signal sequence for protein export. In order to restore the function of the gene it is necessary for an insert to have a defined size (3n+2; n=0, 1, 2, 3 . . . ). In order to express a defined protein sequence as fusion protein of the gene III product it is necessary in addition for both the 3' and the 5' junction to be in the correct reading frame, and for the corresponding insert to be present in the correct orientation. This therefore applies overall to only about every 18th (3×3×2) HPV DNA-containing recombinants. A small portion thereof is in turn inactivated by translation stop codons present in the insert or by proteins which are not functional because of their folding. Because of the stated parameters it is difficult to estimate what is the minimum number of recombinants necessary to express with great probability any required part of an HPV genome as fd fusion protein in the phage bank. In papillomaviruses about 10 kb of the genome (partly by overlapping open reading frames) code for proteins. Of 2000 tetracycline-resistant insert-harboring recombinants, about 100 (1/18) clones express HPV sequences in a suitable manner. With average HPV fragment sizes of 50–150 bp, the expressed HPV sequence amounts to about 5000–15000 bp. In fact fd banks with about 2000 recombinants prove to be sufficiently representative.

In order to ensure the specificity of the immunoscreening, either several different recombinants of a seroreactive region or at least several identical but independently isolated phage recombinants were always isolated.

The amino-acid position indicators in FIGS. 2 and 5 hereinafter relate to the E1 and E2 proteins and not to the positions of the open reading frames. The first methionine was given position 1.

EXAMPLE 1

Preparation of polyclonal antisera against HPV 16 E1

In order to isolate seroreactive phage recombinants from the HPV 16 fd expression bank, initially polyclonal rabbit sera against HPV 16 E1 MS2 fusion proteins were prepared. For this, the Pst I A fragment of HPV 16 (bp 875–3693) was cloned into the Pst I cleavage site of the expression vector pEX12mer (Seedorf et al., EMBO J. 6, 139–144, 1987), by which amino acids 5–649 of HPV 16 E1 ORF are expressed (FIG. 1). This vector is a derivative of the plasmid pPLC24 (Remaut et al., Gene 15, 81–93, 1981) which has been modified by insertion of the pUC8 polylinker behind the MS2 polymerase portion. The fusion protein is transcribed in the pEX12mer by the temperature-inducible lambda pL promoter. The N-terminal fusion portion of the MS2 protein amounts to 100 amino acids.

Since the original HPV 16 isolate (Seedorf et al., Virology, 145, 181–185, 1985) has a reading frame mutation in the region of the E1 open reading frame (nucleotide position 1138), recourse was had to an HPV 16 isolate from a cervical carcinoma with a complete E1 ORF. Because of the selected restriction cleavages, the HPV 16 E1 open reading frame (bp 865–2811) is thus completely expressed apart from three N-terminal amino acids.

The clonings and plasmid analyses were initially carried out using the E. coli strain W6 in which there is constitutive expression of the repressor for the lambda promoter. This prevented expression of the fusion proteins, in order to prevent counterselection after the transformations. After examination of the cloning by restriction analysis, and Southern blot hybridization with radioactive labelled HPV 16 DNA (Pst I A fragment), the plasmid DNA of the construct was used for transformation in E. coli N6045. This strain is able, because of its temperature-sensitive repressor of the lambda promoter, to express the MS2 fusion proteins.

It was then possible in a Western blot to examine, with the aid of a monoclonal antibody directed against the MS2 portion of the fusion protein, by comparison of extracts from induced and non-induced bacteria the size and the expression rate of the fusion protein. Since the band of the MS2 E1 fusion protein corresponded to the expected size of about 90 kD, no examination of the cloning junctions by sequencing was carried out. In the two other reading frames of the HPV 16 Pst I A fragment, expression of larger proteins is impossible because of the presence of translation stop codons. In addition, both Pst I cleavage sites of the vector-insert junctions were retained. Correct expression of the E1 open reading frame was confirmed by the results of the immuno-screening of the HPV 16 fd expression banks, which are described in the following section.

The MS2-E1 fusion protein was then purified from induced E. coli cultures by differential extraction and by electroelution from SDS polyacrylamide gels, and was then used to immunize two rabbits.

EXAMPLE 2

Identification of seroreactive regions on the HPV 16 E1 protein

Both of the polyclonal rabbit sera prepared against HPV 16 E1 were used to examine five different HPV 16 fd expression banks for reactive recombinants. It was possible in this way to identify a total of at least two different antibody binding sites represented by non-overlapping phage clones. In total, 19 independent phage clones which contain seven different classes of HPV 16 inserts were isolated (FIG. 2). Six classes have a common overlapping region which codes for the HPV 16 E1 specific peptide EDLVDFIVND (SEQ ID NO:23). The second identified epitope on the E1 protein is represented by a recombinant phage (clone 1059) which codes for the E1 peptide GSPLSDIS (SEQ ID NO:7).

The original HPV 16 isolate has a reading frame mutation in the E1 open reading frame (nucleotide position 1138). The DNA of this HPV 16 isolate was used to prepare the fd expression banks. Two of the isolated seroreactive fd recombinants contain this region and therefore also have the reading frame mutation. In clone 1145 this leads to a change of reading frame, and this results in C-terminal attachment of three HPV 16-E2 non-specific amino acids ( . . . ValValHis). Clone 1059 starts in the wrong frame and is converted into the correct HPV 16 E1 reading frame by the reading frame mutation of the HPV 16 isolate used. The clone codes for the peptide STGSKTKVFGSPLKSDIS (SEQ ID NO:24), (SEQ ID NO:7) of which only the C-terminal amino acids . . . GSPLSDIS derive from the actual HPV 16 E1 protein and must form the epitope.

Both clones which contain the reading frame mutation have the correct insert size (3n+2 base pairs) to restore the reading frame of gene III of the phage vector.

EXAMPLE 3

Preparation of polyclonal antisera against HPV 16 E2

Like the case of the HPV 16 E1 open reading frame, no suitable antisera were available for the HPV 16 E2 protein either. For this reason, the HPV 16 E2 open reading frame (nucleotide position 2756–3850; AA 1–365) was expressed in the-vector pEX12mer as already described for the E1 protein.

Firstly the HPV 16 DNA fragment was cloned via the Hinf I cleavage site at position 2761 into the pEX12mer vector. In this case the starting material was an already sub-cloned HPV 16 fragment (bp 2367–4467). This fragment was cut out of the vector again, via the additionally inserted non-HPV 16-specific restriction sites Xba I (5' end) and Bam HI (3' end), and prepared. This DNA fragment which is 2.1 kb in size (Xba I/Bam HI) was then partially cut with Hinf I. This results, inter alia, in a fragment which is 1700 bp in size between the 3'-terminal Ban HI cleavage site and Hinf I site at bp 2761. The internal Hinf I cleavage site (bp 3539) in this fragment is uncleaved, and the HPV 16 E2 ORF is completely present apart from three amino-terminal amino acids. After preparation, the Hinf/Bam fragment was cloned into the pEX12mer expression vector which had been cleaved with Bam HI. This resulted, via the compatible Bam HI sites, in linear products of vector and insert. The free ends of these products were filled in with Klenow polymerase and then closed by ligation. This results in an MS2-E2 junction at the filled-in cleavage sites Bam HI (vector) and Hinf I (E2 insert) with loss of the two restriction sites. Using Eco RI/Bam HI double restriction cleavages it was possible to identify recombinants which harboured the HPV 16 E2 fragment in the correct orientation.

After transformation into the E. coli expression strain 6045 it was not possible using a monoclonal antibody directed against the MS2 polymerase to find any production whatever of the MS2 fusion protein. In order to rule out a displacement of the reading frame at the MS2-E2 junction, the plasmid DNA of a total of 16 different MS2-E2 recombinants was hybridized in a Southern blot with an oligo-nucleotide derived from the correct Ban HI/Hinf I junction. Since an unambiguous hybridization signal was identifiable with 15 clones, it was assumed that the cloning had taken place in the correct reading frame, and expression of the complete E2 ORP is not possible in pEX vectors. As a substitute, the HPV 16 E2 protein was then expressed in two halves in the pEX12mer vector.

EXAMPLE 4

Expression of the amino-terminal region of HPV 16 E2

The amino-terminal region of the E2 open reading frame between nucleotide position 2761 and 3209 was cloned into the pex12mer vector and expressed. Since the E2 open reading frame starts at nucleotide position 2756, the MS2-E2 fusion protein lacks the first two amino acids (Met-Glu) of the E2 protein (FIG. 4).

Plasmid DNA composed of pEX12mer and HPV 16 E2, which were obtained from the cloning described above, was truncated at the carboxyl terminus by deletion of a Hinc II (HPV 16 bp 3209)/Bam HI fragment and religation (blunt/flush from Hinc II and Bam HI). This results in expression of the N-terminal part of HPV 16 E2 between nucleotide position 2761 (Hinf I) and 3209 (Hinc II). A fusion protein about 30 kD in size was detectable in induced bacteria in a Western blot with an anti-MS2 molecule antibody.

The fusion protein was purified by differential extraction of the induced bacterial lysate and by electroelution of the protein band from SDS polyacrylamide gels stained with Coomassie blue, and used for immunizing rabbits.

EXAMPLE 5
Expression of the carboxyl-terminal region of HPV 16 E2

The C-terminal region of the HPV 16 E2 open reading frame between nucleotide position 3209 and 3850 was expressed in the pEX12mer vector (FIG. 3). The region is thus directly connected to the expressed amino-terminal part, described above, of the HPV16 E2 open reading frame.

For this, recourse was had to the Xba/Bam fragment which has been described above and which contains the complete HPV 16 E2 reading frame. After restriction cleavage, a Hinc II/Bam HI fragment (nucleotide position 3209–4467) which contains the carboxyl-terminal half of HPV 16 E2 was isolated. This fragment was inserted into the Bam HI cleavage site of the pEX12mer expression vector (5'Bam HI/Hinc II—Bam HI/Bam HI 3'). It was possible with the aid of the anti-MS2 monoclonal antibody to identify in extracts of induced bacteria a fusion protein of about 30 kD, which was purified by differential extraction and electroelution from SDS polyacrylamide gels, and was used to immunize rabbits.

EXAMPLE 6
Identification of seroreactive regions on the HPV 16 E2 protein

Available for the immunoscreening of the fd HPV 16 expression banks was a total of four different anti-HPV 16 E2 antisera: in each case two sera against the amino-terminal part (bp 2761–3209; AA 3–152) and two against the carboxyl-terminal part of the E2 (bp 3209–3850; AA 153–365) open reading frame. These sera were used to examine five different expression banks for seroreactive recombinants. This resulted in isolation of a total of 32 clones, of which 26 contain amino-terminal sequences of the E2 protein. These 26 clones form a total of 11 different classes which represent four different non-overlapping regions (FIG. 5).

All the epitopes are located in a restricted region comprising 88 amino acids of the amino terminus of the E2 open reading frame which is located between nucleotide position 2792 (AspLysIle . . . ) and 3055 ( . . . SerLeuGlu).

It was possible to locate in the carboxyl-terminal region at least two independent non-overlapping epitopes (TSVFSSNEVSSPEII (SEQ ID NO:19) and TEETQTTIQRPRISEPDTGN (SEQ ID NO:22), FIG. 5). These are represented by a total of four classes of recombinants with six independent isolates. The region of the E2 open reading frame which is covered by the clones is located between nucleotide position 3343 (ThrSerVal . . . ) and 3502 ( . . . ThrGlyAsn) and comprises 52 amino acids.

Five classes of recombinants (12 isolates) extend over nucleotide position 2926. All the clones have a point mutation (A→G transition) here, but this does not lead to a change in the corresponding amino acid (glutamine).

EXAMPLE 7
Immunoscreening of fd phase expression banks

1. Phage affinity concentration with protein A-Sepharose columns

The phage banks prepared in the fd phage expression system used unavoidably underwent amplification on cloning. The extent of this replication of the original clones is in turn greatly influenced by the nature of the individual recombinants, for example by different sizes of inserts or conformation of the coat proteins, inhibition of physiological processes in the infected bacteria and many others, and it was therefore not to be expected that uniform amplification of all phages takes place. In order to isolate underrepresented phage recombinants or clones from large libraries, seroreactive phage recombinants were concentrated. For this, use was made of the circumstance that the foreign sequences expressed in each case appear as part of an fd gene III fusion protein on the coat of natural phage particles. Large amounts of phages ($10^9$–$10^{12}$ particles) were for this purpose bound to protein A antibody columns and eluted again.

For this, initially protein A-Sepharose was swollen with PBS for 30 min and was washed with PBS. Subsequently the protein A-Sepharose was incubated with about 1 to 2 ml of suitable polyclonal sera (rabbit or human) or with corresponding protein A-binding monoclonal antibodies in Eppendorf reaction tubes on a rotary shaker at 4° C. for 1 to 2 days. Subsequently the protein A-Sepharose was washed 10 times by the Sepharose being alternately resuspended in 10 ml of PBS and pelleted again by centrifugation (2 min, 6000 rpm). The protein A-Sepharose-IgG complexes formed were then incubated with an appropriate amount of phages as above. Then the Sepharose was washed with PBS several times as before and packed into a Pasteur pipette closed with a glass bead and washed with several liters (2–15 l) flowing through. The column material was removed and then incubated in the same volume of elution buffer (1 mg/ml BSA, 0.1 M HCl, glycine, pH 2.2) for 15 min. After brief centrifugation the supernatant, which now contains free phages and antibodies, was neutralized with ⅕ of the volume of tris base (0.5 M). Antibodies which recognize the recombinant gene are able to inhibit binding of the phage to the bacterial cells and thus the cycle of infection. For this reason the phages were added in 100–200 µl aliquots of the eluates immediately after neutralization to exponentially growing *E. coli* K91 and plated out on complete medium plates. It emerged during the work that replica filters of these phage platings were unsuitable for immunoblotting, probably because of contaminants in the eluate. For this reason the resulting plaques were again rinsed off the plates with complete medium and subsequently plated out from the phage suspensions obtained in this way, which had undergone renewed amplification, and the immunoblotting was carried out on minimal agar plates.

2. Phage Platings and preparation of nitrocellulose replica filters for the immunoblotting All the fd phage derivatives were plated out on a lawn formed by *E. coli* K91 (Lyons and Zinder, Virology, 49, 45–60, 1972). This strain is distinguished by a large number of F pili (5 per cell, compared with about 0.5 per cell in most F+ strains) which are responsible for uptake of filamentous phages. This is particularly important for the fd expression system used in this study because the recombinant fuse phages have, owing to the uptake of a part of the Tn10 transposon (tetracycline resistance), a genome which is distinctly enlarged compared with the wild-type, and for this reason form particularly small plaques.

To plate out the phages, a K91 overnight culture was diluted 1:100 in complete medium (2× YT) and incubated at 37° C. for 3 to 4 h. After a density of $E_{600}$=0.8–1.2 was reached, 200 μl of the bacteria were plated out with an appropriate amount of phages, together with 3.5 ml of agarose (0.6% agarose, 10 mM $MgSO_4$, 50° C.) on pre-warmed bacteria plates. Minimal agar plates were always used for every plating intended to be used for nitrocellulose replicas for the immunoscreening. Platings out for determination of the phage titer or for DNA hybridization were carried out on complete medium plates.

Use of complete medium plates for the immunoblotting always lead to very high non-specific reactivity of the filters with the sera used.

The plates were incubated at 37° C. overnight. After about 16 hours, a nitrocellulose filter was placed on for 10–15 min, marked with four asymmetric pricks with a needle and removed again using flat-ended forceps. The filters were labelled and then inverted onto a fresh minimal agar plate and incubated further at 37° C. for 5–6 hours. This increased the amount of phage particles (proteins) on the filter since the reincubation makes it possible for the bacteria and phages bound to the filters to grow further via the nutrients diffusing from the plate. Subsequently the filters were removed and saturated in 10% milk (skim milk powder in PBS) for 30–60 min. The filters were then incubated with suitable dilutions of appropriate sera in 5% milk at 4° C. overnight.

3. Immunostaining of replica filters and cloning of reactive recombinants

After removal of the replica filters, blocking in 10% milk (in PBS) for 60 min and overnight incubation with antisera, the nitrocellulose filters were washed in PBS, 0.05% Tween 20 (5 changes of washing buffer) for 30 min. The filters were then incubated with 1:1000 dilutions of appropriate second antibodies (peroxidase-coupled goat anti-human, anti-rabbit or anti-mouse) in 5% milk at RT for 2 h. This was followed by renewed washing (see above) and incubation in the following staining mixture:

40 mg of diaminobenzidine

30 μl of 30% $H_2O_2$ 1.5 ml of 1% $NiSO_4$ in 50 ml of PBS

After sufficient color had developed, the filters were removed from the solution, placed in water for 30 min and then dried on 3 MM paper.

The prick holes and signals on the filters were then copied onto a sheet or the lid of a bacteria dish. This made it possible to assign a position or, if the phage dilution was sufficiently large (round 2 or higher), a plaque to a signal. A sterile toothpick was gently stabbed into the position or the plaque, and the toothpick was placed in 500 μl of complete medium for 10–15 min. This phage suspension then contained generally about $10^{6-10^7}$ infectious particles, which comprises about 0.1–1% of the phages in a plaque. The phage suspensions were then incubated at 65° C. for 15–20 min in order to kill bacteria which had been carried over, and were then stored at 4° C.

DESCRIPTION OF THE FIGURES

FIG. 2 Seroreactive regions on the HPV 16 E1 protein. The figure includes amino acid sequences SEQ ID NO:1, SEQ ID NO:2, SEQ ID NO:3, SEQ ID NO:4, SEQ ID NO:5, SEQ ID NO:6, and SEQ ID NO:24. Small letters indicate the amino acids of clones 1145 and 1059 which, because of the change in reading frame of the HPV 16 isolate used for cloning the fd banks, are not derived from the HPV 16 E1 protein (see text). Clones 1090, 1079, 1084, 1029, 1099 and 1145 have a common region of 10 amino acids (EDLVDFIVND) (SEQ ID NO:23) which possibly represents a common epitope of the clones, although other antibody binding sites on these clones cannot be ruled out. Clone 1059 has, because of the change in reading frame, no common amino-acid sequences with the other clones, although the insert of this clone overlaps with the insert of clone 1145. The position indications relate to the HPV 16 E1 open reading frame. The amino acids of clones 1145 and 1059 which do not derive from E1 are not taken into account here.

FIG. 5 Seroreactive regions on the HPV 16 E2 protein. The figure includes amino acid sequences SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. The regions (E2-1066, -1170, -1074, -1112) on the carboxyl-terminal half of HPV 16 E2 are all located in a region 88 amino-acids long (between AA 13 and 100) and partially overlap. The carboxyl-terminal regions are also closely adjacent (between AA 197 and 249). The two regions are in each case arranged approximately proportional to their position on the E2 protein.

Figure 1:
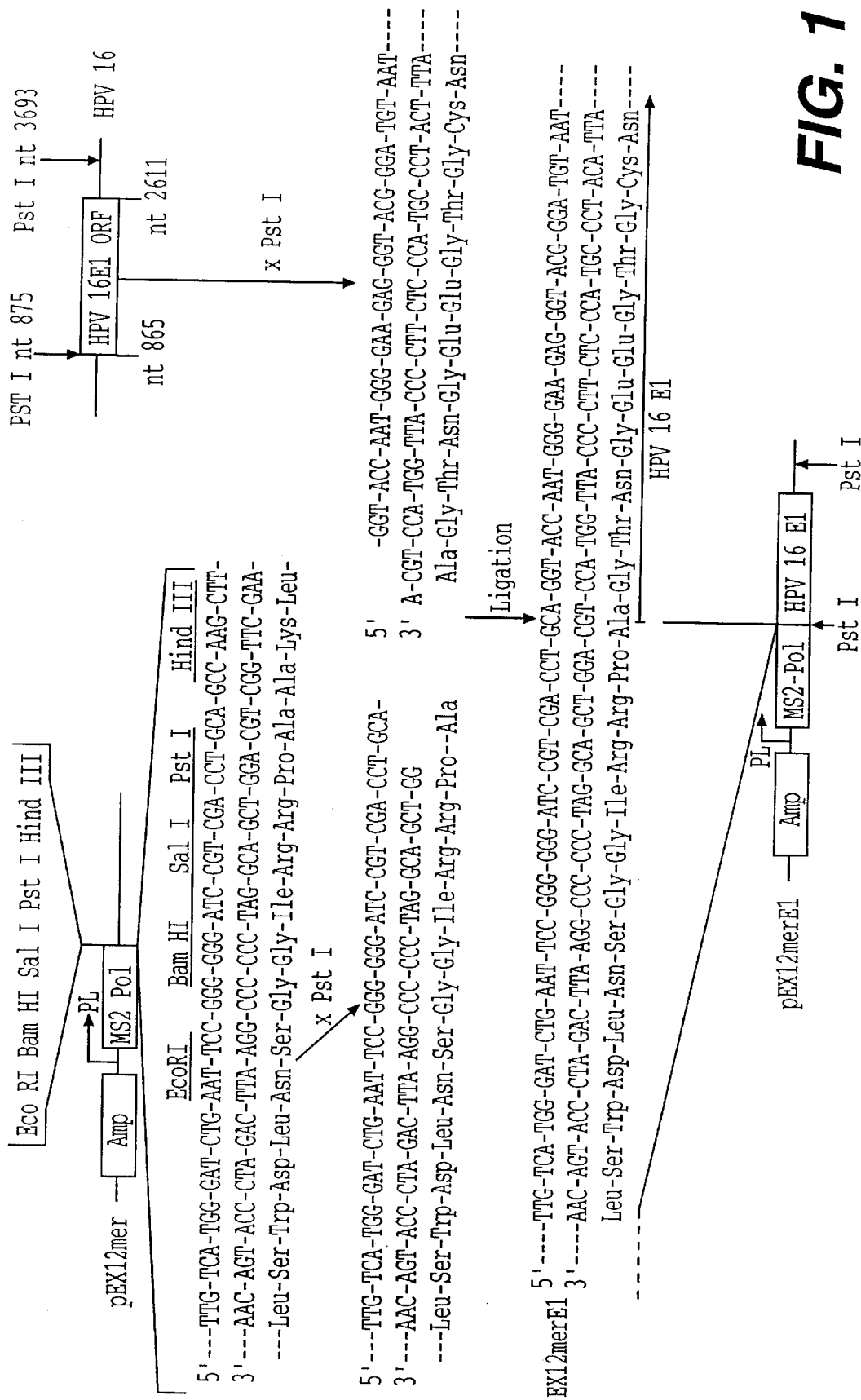
FIG. 1 Cloning of the E1 open reading frame into the expression vector pEX12mer. The figure includes DNA sequences SEQ ID NO:25, SEQ ID NO:27, SEQ ID NO:29, SEQ ID NO:31, and amino acid sequences SEQ ID NO:26, SEQ ID NO:28, SEQ ID NO:30, and SEQ ID NO:32.
Figure 3:
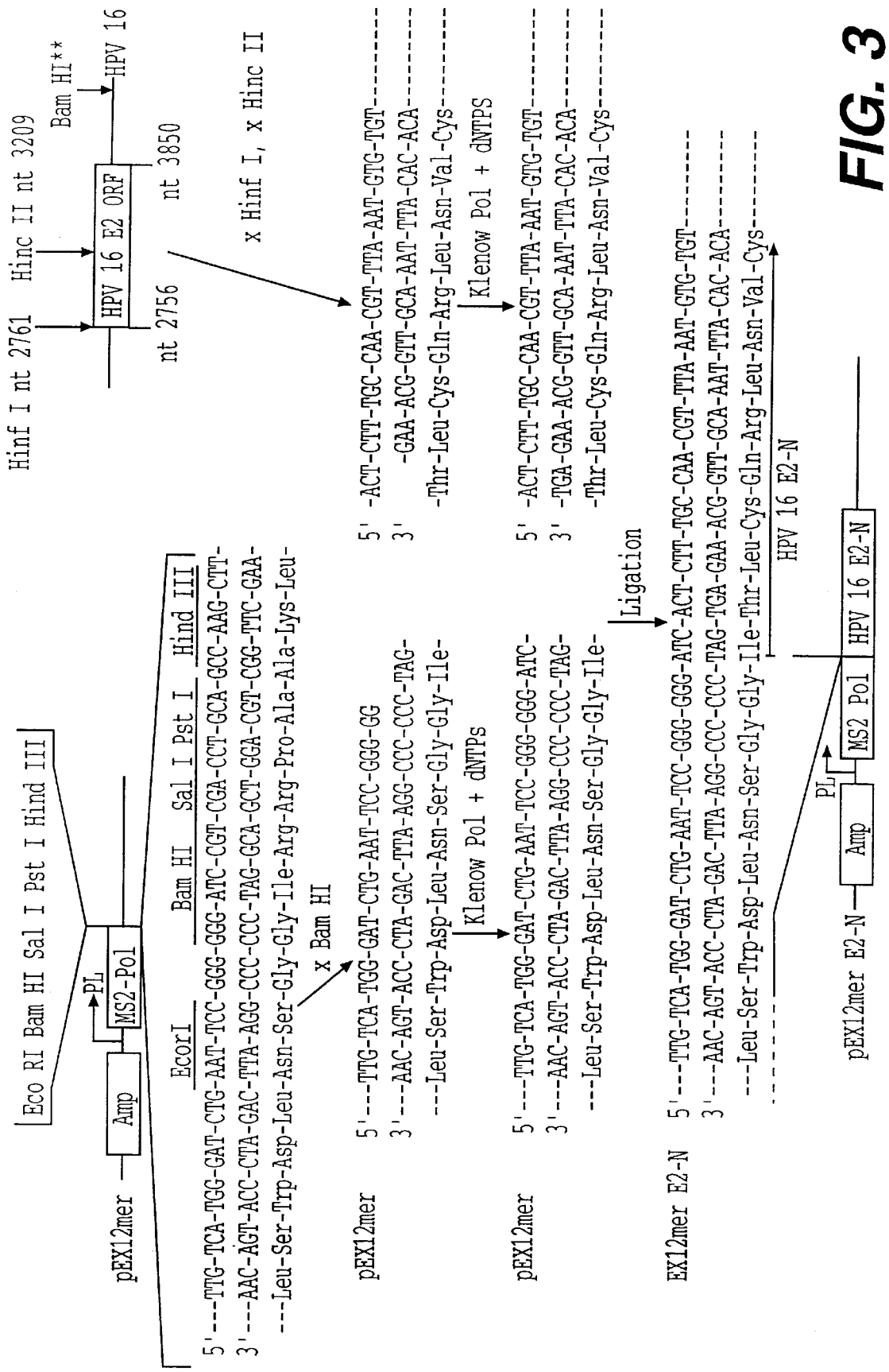
FIG. 3 Cloning of the carboxyl-terminal half of the HPV 16 E2 protein into the expression vector pEX12mer. The figure includes DNA sequences SEQ ID NO:25, SEQ ID NO:33, SEQ ID NO:35, SEQ ID NO:37, SEQ ID NO:39, and amino acid sequences SEQ ID NO:26, SEQ ID NO:34, SEQ ID NO:36, SEQ ID NO:38, and SEQ ID NO:40.
Figure 4:
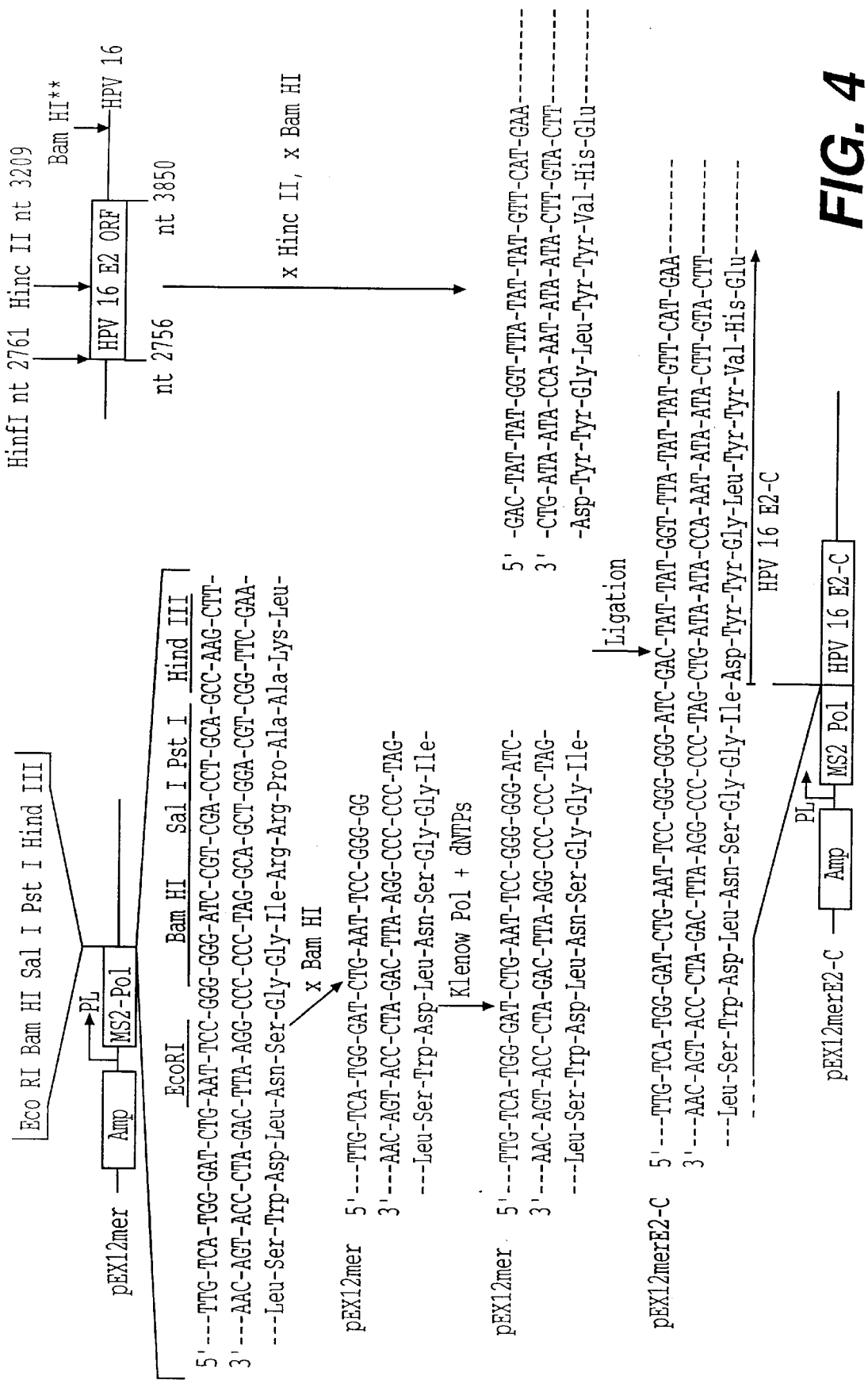
FIG. 4 Cloning of the amino-terminal half of the HPV 16 E2 protein into the expression vector pEX12mer. The figure includes DNA sequences SEQ ID NO:25, SEQ ID NO:33, SEQ ID NO:35, SEQ ID NO:41, SEQ ID NO:43 and amino acid sequences SEQ ID NO:26, SEQ ID NO:34, SEQ ID NO:36, SEQ ID NO:42, and SEQ ID NO:44.

What is claimed is:

1. A peptide consisting of a sequence selected from the group consisting of:
NGWFYVEAVVEKKTGDAISDDENENDSDTGEDLVDFIVNDNDYLT (SEQ ID NO:1),
NENDSDTGEDLVDFIVND (SEQ ID NO:2),
MADPAGTNGEEGTGCNGWFYVEAVVEKKTGDAISSDDENENDSDTGEDLVDFIVNDNDYLT (SEQ ID NO:3),
EDLVDFIVNDNDYLT (SEQ ID. NO:4),
EDLVDFIVNDNDYLTQAETETAHALFTAQEAKQH (SEQ ID NO:5),
NENDSDTGEDLVDFIVNDNDYLTQAETETAHALFTAQEAKQHRDAVQVLKRKYL (SEQ ID NO:6), and
GSPLSDIS (SEQ ID NO:7).

2. A composition comprising:
1) a peptide as claimed in claim 1, and
2) a carrier.

3. A composition for diagnostic purposes for identifying specific antibodies against HPV 16 E1 protein, comprising a peptide selected from the group as claimed in claim 1.

4. The peptide of claim 1, wherein said peptide is NGWFYVEAVVEKKTGDAISDDENENDSDTGEDLVDFIVNDNDYLT (SEQ ID NO: 1).

5. The peptide of claim 1, wherein said peptide is NENDSDTGEDLVDFIVND (SEQ ID NO:2).

6. The peptide of claim 1, wherein said peptide is MADPAGTNGEEGTGCNGWFYVEAVVEKKTGDAISSDDENENDSDTGEDLVDFIVNDNDYLT (SEQ ID NO:3).

7. The peptide of claim 1, wherein said peptide is EDLVDFIVNDNDYLT (SEQ ID NO:4).

8. The peptide of claim 1, wherein said peptide is EDLVDFIVNDNDYLTQAETETAHALFTAQEAKQH (SEQ ID NO:5).

9. The peptide of claim 1, wherein said peptide is NENDSDTGEDLVDFIVNDNDYLTQAETETAHALFTAQEAKQHRDAVQVLKRKYL (SEQ ID NO:6).

10. The peptide of claim 1, wherein said peptide is GSPLSDIS (SEQ ID NO:7).

11. A peptide comprising an amino acid sequence selected from the group consisting of:
NGWFYVEAVVEKKTGDAISDDENENDSDTGEDLVDFIVNDNDYLT (SEQ ID NO:1),
NENDSDTGEDLVDFIVND (SEQ ID NO:2),
EDLVDFIVNDNDYLT (SEQ ID. NO:4),
EDLVDFIVNDNDYLTQAETETAHALFTAQEAKQH (SEQ ID NO:5),
NENDSDTGEDLVDFIVNDNDYLTQAETETAHALFTAQEAKQHRDAVQVLKRKYL (SEQ ID NO:6), and
GSPLSDIS (SEQ ID NO:7),
wherein the peptide comprises only one epitope of the E1 protein of herpesvirus 16 (HPV 16).

12. A composition comprising:
1) the peptide of claim 11, and
2) a carrier.

13. A composition for diagnostic purposes for identifying specific antibodies against HPV 16 E1 protein, comprising the peptide of claim 11.

14. The peptide of claim 11, which comprises NGWFYVEAVVEKKTGDAISDDENENDSDTGEDLVDFIVNDNDYLT (SEQ ID NO: 1).

15. The peptide of claim 11, which comprises NENDSDTGEDLVDFIVND (SEQ ID NO:2).

16. The peptide of claim 11, which comprises EDLVDFIVNDNDYLT (SEQ ID NO:4).

17. The peptide of claim 11, which comprises EDLVDFIVNDNDYLTQAETETAHALFTAQEAKQH (SEQ ID NO:5).

18. The peptide of claim 11, which comprises NENDSDTGEDLVDFIVNDNDYLTQAETETAHALFTAQEAKQHRDAVQVLKRKYL (SEQ ID NO:6).

19. The peptide of claim 11, which comprises GSPLSDIS (SEQ ID NO:7).

20. A fusion protein comprising the peptide of claim 11.

21. A composition comprising the fusion protein of claim 20.

22. A peptide comprising an epitope of the HVP 16 E1 protein, said peptide comprising an amino acid sequence selected from the group consisting of:
NGWFYVEAVVEKKTGDAISDDENENDSDTGEDLVDFIVNDNDYLT (SEQ ID NO: 1),
NENDSDTGEDLVDFIVND (SEQ ID NO:2),
MADPAGTNGEEGTGCNGWFYVEAVVEKKTGDAISSDDENENDSDTGEDLVDFIVNDNDYLT (SEQ ID NO:3),
EDLVDFIVNDNDYLT (SEQ ID NO:4),
EDLVDFIVNDNDYLTQAETETAHALFTAQEAKQH (SEQ ID NO:5),
NENDSDTGEDLVDFIVNDNDYLTQAETETAHALFTAQEAKQHRDAVQVLKRKYL (SEQ ID NO:6), and
GSPLSDIS (SEQ ID NO:7),
wherein the peptide comprises no other epitopes of the HPV 16 E1 protein.

23. A composition comprising:
1) the peptide of claim 22, and
2) a carrier.

24. A composition for diagnostic purposes for identifying specific antibodies against HPV E1 protein, said composition comprising the peptide of claim 23.

25. The peptide of claim 22, which comprises NGWFYVEAVVEKKTGDAISDDENENDSDTGEDLVDFIVNDNDYLT (SEQ ID NO:1).

26. The peptide of claim 22 which comprises NENDSDTGEDLVDFIVND (SEQ ID NO:2).

27. The peptide of claim 22, which comprises MADPAGTNGEEGTGCNGWFYVEAVVEKKTGDAISSDDENENDSDTGEDLVDFIVNDNDYLT (SEQ ID NO:3).

28. The peptide of claim, which comprises EDLVDFIVNDNDYLT (SEQ ID NO:4).

29. The peptide of claim 23, which comprises EDLVDFIVNDNDYLTQAETETAHALFTAQEAKQH (SEQ ID NO:5).

30. The peptide of claim 23, which comprises NENDSDTGEDLVDFIVNDNDYLTQAETETAHALFTAQEAKQHRDAVQVLKRKYL (SEQ ID NO:6).

31. The peptide of claim 23, which comprises GSPLSDIS (SEQ ID NO:7).

32. A fusion protein comprising the peptide of claim 23.

33. A composition comprising the fusion protein of claim 32.

34. A peptide comprising an amino acid sequence selected from the group consisting of:
NGWFYVEAVVEKKTGDAISDDENENDSDTGEDLVDFIVNDNDYLT (SEQ ID NO:1),
NENDSDTGEDLVDFIVND (SEQ ID NO:2),
MADPAGTNGEEGTGCNGWFYVEAVVEKKTGDAISSDDENENDSDTGEDLVDFIVNDNDYLT (SEQ ID NO:3),
EDLVDFIVNDNDYLT (SEQ ID NO:4),
EDLVDFIVNDNDYLTQAETETAHALFTAQEAKQH (SEQ ID NO: 5), and
NENDSDTGEDLVDFIVNDNDYLTQAETETAHALFTAQEAKQHRDAVQVLKRKYL (SEQ ID NO:6),
wherein said peptide does not comprise the sequence GSPLSDIS (SEQ ID NO:7).

35. A composition comprising:
1) the peptide of claim 34, and
2) a carrier.

36. A composition for diagnostic purposes for identifying specific antibodies against HPV E1 protein, said composition comprising the peptide of claim 35.

37. The peptide of claim 35, which comprises NGWFYVEAVVEKKTGDAISDDENENDSDTGEDLVDFIVNDNDYLT (SEQ ID NO:1).

38. The peptide of claim 35, which comprises NENDSDTGEDLVDFIVND (SEQ ID NO:2).

39. The peptide of claim 35, which comprises MADPAGTNGEEGTGCNGWFYVEAVVEKKTGDAISSDDENENDSDTGEDLVDFIVNDNDYLT (SEQ ID NO:3).

40. The peptide of claim 35, which comprises EDLVDFIVNDNDYLT (SEQ ID NO:4).

41. The peptide of claim 35, which comprises EDLVDFIVNDNDYLTQAETETAHALFTAQEAKQH (SEQ ID NO:5).

42. The peptide of claim 35, which comprises NENDSDTGEDLVDFIVNDNDYLTQAETETAHALFTAQEAKQHRDAVQVLKRKYL (SEQ ID NO:6).

43. A fusion protein comprising the peptide of claim 35.

44. A composition comprising the fusion protein of claim 43.

* * * * *

UNITED STATES PATENT AND TRADEMARK OFFICE
CERTIFICATE OF CORRECTION

PATENT NO. : 6,221,577 B1  
DATED : April 24, 2001  
INVENTOR(S) : Martin Müller et al.

It is certified that error appears in the above-identified patent and that said Letters Patent is hereby corrected as shown below:

<u>Title page,</u>  
Item [57],ABSTRACT,  
Line 1, "protein" should read -- proteins --.

<u>Column 31,</u>  
Line 28, "claim 23" should read -- claim 22 --.  
Line 38, after "claim", insert -- 22 --.  
Line 40, "claim 23" should read -- claim 22 --.  
Line 43, "claim 23" should read -- claim 22 --.  
Line 46, "claim 23" should read -- claim 22 --.  
Line 48, "claim 23" should read -- claim 22 --.

<u>Column 32,</u>  
Line 26, "claim 35" should read -- claim 34 --.  
Line 27, "claim 35" should read -- claim 34 --.  
Line 30, "claim 35" should read -- claim 34 --.  
Line 32, "claim 35" should read -- claim 34 --.  
Line 36, "claim 35" should read -- claim 34 --.  
Line 38, "claim 35" should read -- claim 34 --.  
Line 41, "claim 35" should read -- claim 34 --.  
Line 44, "claim 35" should read -- claim 34 --.

Signed and Sealed this

Thirtieth Day of July, 2002

*Attest:*

*Attesting Officer*

JAMES E. ROGAN  
*Director of the United States Patent and Trademark Office*

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:

(A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:1:

Asn Gly Trp Phe Tyr Val Glu Ala Val Val Glu Lys Lys Thr Gly Asp
1               5                  10                  15

Ala Ile Ser Asp Asp Glu Asn Glu Asn Asp Ser Asp Thr Gly Glu Asp
            20                  25                  30

Leu Val Asp Phe Ile Val Asn Asp Asn Asp Tyr Leu Thr
        35                  40                  45

(2) INFORMATION FOR SEQ ID NO:2:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:2:

Asn Glu Asn Asp Ser Asp Thr Gly Glu Asp Leu Val Asp Phe Ile Val
1               5                  10                  15

Asn Asp (2) INFORMATION FOR SEQ ID NO:3:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (xi) SEQUENCE DESCRIPTION: SEQ ID NO:3:

Met Ala Asp Pro Ala Gly Thr Asn Gly Glu Glu Gly Thr Gly Cys Asn
1               5                  10                  15

Gly Trp Phe Tyr Val Glu Ala Val Val Glu Lys Lys Thr Gly Asp Ala
            20                  25                  30

Ile Ser Asp Asp Glu Asn Glu Asn Asp Ser Asp Thr Gly Glu Asp Leu
        35                  40                  45

Val Asp Phe Ile Val Asn Asp Asn Asp Tyr Leu Thr
    50                  55                  60

(2) INFORMATION FOR SEQ ID NO:4:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:4:

Glu Asp Leu Val Asp Phe Ile Val Asn Asp Asn Asp Tyr Leu Thr
1               5                  10                  15

(2) INFORMATION FOR SEQ ID NO:5:

(i) SEQUENCE CHARACTERISTICS:
        (A) LENGTH: 34 amino acids
        (B) TYPE: amino acid (D) TOPOLOGY: linear (ii) MOLECULE TYPE: peptide (xi) SEQUENCE DESCRIPTION: SEQ ID NO:5:

Glu Asp Leu Val Asp Phe Ile Val Asn Asp Asn Asp Tyr Leu Thr Gln
1               5                   10                  15

Ala Glu Thr Glu Thr Ala His Ala Leu Phe Thr Ala Gln Glu Ala Lys
                20                  25                  30

Gln His (2) INFORMATION FOR SEQ ID NO:6:

(i) SEQUENCE CHARACTERISTICS:
        (A) LENGTH: 54 amino acids
        (B) TYPE: amino acid
        (D) TOPOLOGY: linear (ii) MOLECULE TYPE: peptide (xi) SEQUENCE DESCRIPTION: SEQ ID NO:6:

Asn Glu Asn Asp Ser Asp Thr Gly Glu Asp Leu Val Asp Phe Ile Val
1               5                   10                  15

Asn Asp Asn Asp Tyr Leu Thr Gln Ala Glu Thr Glu Thr Ala His Ala
                20                  25                  30

Leu Phe Thr Ala Gln Glu Ala Lys Gln His Arg Asp Ala Val Gln Val
            35                  40                  45

Leu Lys Arg Lys Tyr Leu
        50

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:7:

Gly Ser Pro Leu Ser Asp Ile Ser
1               5

(2) INFORMATION FOR SEQ ID NO:8:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:8:

Asp Lys Ile Leu Thr His Tyr Glu Asn Asp Ser
1               5                   10

(2) INFORMATION FOR SEQ ID NO:9:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:9:

```
Asp Lys Ile Leu Thr His Tyr Glu Asn Asp Ser Thr Asp Leu Arg Asp
1               5                   10                  15

His Ile
```

(2) INFORMATION FOR SEQ ID NO:10:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:10:

```
Asp Leu Arg Asp His Ile Asp Tyr Trp Lys His
1               5                   10
```

(2) INFORMATION FOR SEQ ID NO:11:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:11:

```
Ala Ile Tyr Tyr Lys Ala Arg Glu Met Gly Phe Lys His Ile Asn His
1               5                   10                  15

Gln Val Val Pro Thr Leu Ala
            20
```

(2) INFORMATION FOR SEQ ID NO:12:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:12:

```
Ala Ile Tyr Tyr Lys Ala Arg Glu Met Gly Phe Lys His Ile Asn His
1               5                   10                  15

Gln Val Val Pro Thr Leu Ala Val Ser Lys Asn Lys Ala Leu
            20                  25                  30
```

(2) INFORMATION FOR SEQ ID NO:13:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:13:

```
Tyr Tyr Lys Ala Arg Glu Met Gly Phe Lys His Ile Asn His Gln Val
1               5                   10                  15

Val Pro Thr Leu Ala Val Ser Lys Asn
            20                  25
```

(2) INFORMATION FOR SEQ ID NO:14:

(i) SEQUENCE CHARACTERISTICS:

(A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:14:

Ile Asn His Gln Val Val Pro Thr Leu Ala Val Ser Lys Asn Lys Ala
1               5                  10                  15

Leu Gln Ala Ile
            20

(2) INFORMATION FOR SEQ ID NO:15:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:15:

Ile Asn His Gln Val Val Pro Thr Leu Ala Val Ser Lys Asn Lys Ala
1               5                  10                  15

Leu (2) INFORMATION FOR SEQ ID NO:16:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:16:

Thr Leu Ala Val Ser Lys Asn Lys Ala Leu Gln Ala Ile Glu Leu Gln
1               5                  10                  15

Leu Thr Leu Glu Thr Ile Tyr Asn Ser Gln Tyr Ser Asn Glu Lys Trp
            20                  25                  30

Thr Leu Gln Asp Val
            35

(2) INFORMATION FOR SEQ ID NO:17:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:17:

Gln Leu Thr Leu Glu Thr Ile Tyr Asn Ser Gln Tyr Ser Asn Glu Lys
1               5                  10                  15

Trp Thr Leu Gln Asp Val Ser Leu Glu
            20                  25

(2) INFORMATION FOR SEQ ID NO:18:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:18:

Thr Leu Glu Thr Ile Tyr Asn Ser Gln Tyr Ser Asn Glu Lys
1               5                   10

(2) INFORMATION FOR SEQ ID NO:19:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:19:

Thr Ser Val Phe Ser Ser Asn Glu Val Ser Ser Pro Glu Ile Ile
1               5                   10                  15

(2) INFORMATION FOR SEQ ID NO:20:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:20:

Val Phe Ser Ser Asn Glu Val Ser Ser Pro Glu Ile Ile Arg Gln His
1               5                   10                  15

Leu Ala Asn His Pro Ala Ala Thr His Thr Lys Ala Val Ala Leu Gly
                20                  25                  30

Thr Glu Glu Thr
        35

(2) INFORMATION FOR SEQ ID NO:21:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:21:

Glu Ile Ile Arg Gln His Leu Ala Asn His Pro Ala Ala Thr His Thr
1               5                   10                  15

Lys Ala Val Ala Leu Gly Thr Glu Glu Thr Gln Thr Thr Ile Gln Arg
                20                  25                  30

Pro Arg Ser Glu Pro
        35

(2) INFORMATION FOR SEQ ID NO:22:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:22:

Thr Glu Glu Thr Gln Thr Thr Ile Gln Arg Pro Arg Ser Glu Pro Asp
1               5                   10                  15

Thr Gly Asn (2) INFORMATION FOR SEQ ID NO:23:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:23:

```
Glu Asp Leu Val Asp Phe Ile Val Asn Asp
1               5                   10
```

(2) INFORMATION FOR SEQ ID NO:24:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:24:

```
Ser Thr Gly Ser Lys Thr Lys Val Phe Gly Ser Pro Leu Ser Asp Ile
1               5                   10                  15
Ser
```

(2) INFORMATION FOR SEQ ID NO:25:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:25:

```
TTGTCATGGG ATCTGAATTC CGGGGGGATC CGTCGACCTG CAGCCAAGCT T          51
```

(2) INFORMATION FOR SEQ ID NO:26:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:26:

```
Leu Ser Trp Asp Leu Asn Ser Gly Gly Ile Arg Arg Pro Ala Ala Lys
1               5                   10                  15
Leu
```

(2) INFORMATION FOR SEQ ID NO:27:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:27:

```
TTGTCATGGG ATCTGAATTC CGGGGGGATC CGTCGACCTG CA                   42
```

(2) INFORMATION FOR SEQ ID NO:28:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:28:

```
Leu Ser Trp Asp Leu Asn Ser Gly Gly Ile Arg Arg Pro Ala
1               5                   10
```

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:29:

```
GGTACCAATG GGGAAGAGGG TACGGGATGT AAT                          33
```

(2) INFORMATION FOR SEQ ID NO:30:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:30:

```
Ala Gly Thr Asn Gly Glu Glu Gly Thr Gly Cys Asn
1               5                   10
```

(2) INFORMATION FOR SEQ ID NO:31:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:31:

```
TTGTCATGGG ATCTGAATTC CGGGGGGATC CGTCGACCTG CAGGTACCAA TGGGGAAGAG    60

GGTACGGGAT GTAAT                                                    75
```

(2) INFORMATION FOR SEQ ID NO:32:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:32:

```
Leu Ser Trp Asp Leu Asn Ser Gly Gly Ile Arg Arg Pro Ala Gly Thr
1               5                   10                  15

Asn Gly Glu Glu Gly Thr Gly Cys Asn
```

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:33:

TTGTCATGGG ATCTGAATTC CGGGGG                    26

(2) INFORMATION FOR SEQ ID NO:34:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:34:

Leu Ser Trp Asp Leu Asn Ser Gly Gly Ile
1           5                   10

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:35:

TTGTCATGGG ATCTGAATTC CGGGGGGATC              30

(2) INFORMATION FOR SEQ ID NO:36:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:36:

Leu Ser Trp Asp Leu Asn Ser Gly Gly Ile
1           5                   10

(2) INFORMATION FOR SEQ ID NO:37:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:37:

ACTCTTTGCC AACGTTTAAA TGTGTGT                 27

(2) INFORMATION FOR SEQ ID NO:38:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (xi) SEQUENCE DESCRIPTION: SEQ ID NO:38:

Thr Leu Cys Gln Arg Leu Asn Val Cys
1               5

(2) INFORMATION FOR SEQ ID NO:39:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:39:

TTGTCATGGG ATCTGAATTC CGGGGGGATC ACTCTTTGCC AACGTTTAAA TGTGTGT         57

(2) INFORMATION FOR SEQ ID NO:40:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:40:

Leu Ser Trp Asp Leu Asn Ser Gly Gly Ile Thr Leu Cys Gln Arg Leu
1               5                   10                  15
Asn Val Cys (2) INFORMATION FOR SEQ ID NO:41:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:41:

GACTATTATG GTTTATATTA TGTTCATGAA                                       30

(2) INFORMATION FOR SEQ ID NO:42:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:42:

Asp Tyr Tyr Gly Leu Tyr Tyr Val His Glu
1               5                   10

(2) INFORMATION FOR SEQ ID NO:43:

(i) SEQUENCE CHARACTERISTICS:

```
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:43:

TTGTCATGGG ATCTGAATTC CGGGGGGATC GACTATTATG GTTTATATTA TGTTCATGAA        60

(2) INFORMATION FOR SEQ ID NO:44:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:44:

Leu Ser Trp Asp Leu Asn Ser Gly Gly Ile Asp Tyr Tyr Gly Leu Tyr
1               5                   10                  15

Tyr Val His Glu
            20
```